United States Patent [19]

Sen et al.

[11] Patent Number: 5,393,922
[45] Date of Patent: Feb. 28, 1995

[54] CATALYTIC DIRECT OXIDATION OF HYDROCARBONS TO ACIDS

[75] Inventors: Ayusman Sen; Minren Lin, both of State College, Pa.

[73] Assignee: Gas Research Institute, Chicago, Ill.

[21] Appl. No.: 95,945

[22] Filed: Jul. 22, 1993

[51] Int. Cl.$^6$ .............................................. C07C 51/16
[52] U.S. Cl. .................................... 562/542; 562/544; 562/549
[58] Field of Search ........................ 562/542, 544, 549

[56] References Cited

U.S. PATENT DOCUMENTS

| | | | |
|---|---|---|---|
| 1,916,041 | 6/1933 | Dreyfus | 562/550 |
| 2,922,809 | 1/1960 | Oberdorfer, Jr. | 568/950 |
| 2,926,191 | 2/1960 | Lawson-Hall et al. | 562/549 |
| 3,215,733 | 11/1965 | MacLean | 562/414 |
| 3,284,492 | 11/1966 | Fremery | 562/408 |
| 3,876,694 | 4/1975 | Gaenzler et al. | 562/522 |
| 4,414,409 | 11/1983 | Waller | 560/233 |
| 4,469,886 | 9/1984 | Pesa et al. | 562/522 |
| 4,494,604 | 1/1985 | Shaw | 166/273 |
| 4,665,213 | 5/1987 | Alper et al. | 554/130 |
| 4,681,707 | 7/1987 | Alper et al. | 554/131 |
| 4,681,751 | 7/1987 | Gosser | 423/584 |
| 4,739,107 | 4/1988 | Drent | 560/204 |
| 4,895,682 | 1/1990 | Ellis, Jr. et al. | 562/512.2 |

OTHER PUBLICATIONS

Baerns, M., van der Wiele, K., and Ross, J. R. H., Methane Activation—A Bibliography, Catal. Today, 4, 471–494, (1989).

Pitchai, R. and Klier, K., Partial Oxidation of Methane, Catal. Rev.—Sci. Eng., 28(1), 13–88, (1986).

Hunter, N. R., Gesser, H. D., Morton, L. A. Yarlagadda, P. S., and Fung, D. P. C., Methanol Formation at High Pressure by the Catalyzed Oxidation of Natural Gas and by the Sensitized Oxidation of Methane, Appl. Catal., 57, 45–54, (1990).

Burch, R., Squire, G. D., Tssang, S. C., Direct Conversion of Methane into Methanol, J. Chem. Soc., Faraday Trans. 1, 85(10), 3561–3568, (1989).

Kowalak, S. and Moffat, J. B., Partial Oxidation of Methane Catalyzed by H—Mordenite and Fluorinated Mordenite, Appl. Catal., 36, 139–145, (1988).

Stolarov, I. P., Vargaftik, M. N., Shishkin, D. I., and Moiseev, I.I., Oxidation of Ethane and Propane With Co(II) Catalyst, J. Chem. Soc., Commun., 938–939, (1991).

Vargaftik, M. N., Stolarov, I. P., and Moiseev, I. I., Highly Selective Partial Oxidation of Methane to Methyl Trifluoroacetate, J. Chem. Soc., Chem. Commun., 1049–1050, (1990).

Herron, N., The Selective Partial Oxidation of Alkanes Using Zeolite Based Catalysts, New J. Chem., 13, 761–766, (1989).

Lyons, J. E., Ellis, Jr., P. E., and Durante, V. A., Active Iron Oxo Centers for the Selective Oxidation of Alkanes, Stud. Surf. Sci. Catal., 67, 99–116, (1991).

Periana, R. A., Taube, D. J., Evitt, E. R., Loffler, D. G., Wentrcek, P. R., Voss, G. and Masuda, T., A Mercury—Catalyzed, High—Yield System for the Oxidation of Methane to Methanol, Science, 259, pp. 340–343, (1933).

Horvath, I. T., Cook, R. A., Miller, J. M. and Kiss, G., Low—Temperature Methane Chlorination with Aqueous Platinum Chlorides in the Pressence of Chlorine, Organometallics, 12, pp. 8–10, (1993).

Merzouki, M., Taouk, B., Monceaux, L., Bordes, E. and Courtine, P., Catalytic Properties of Promoted Vana- (List continued on next page.)

Primary Examiner—José G. Dees
Assistant Examiner—Joseph M. Conrad
Attorney, Agent, or Firm—Speckman, Pauley & Fejer

[57] ABSTRACT

A process for catalytic direct oxidation of hydrocarbons, particularly lower alkanes and single ring aromatics, to acids by dioxygen under mild temperature conditions using specified metal or metal salt catalysts. Turnovers in excess of 1000 for acetic acid formation from ethane and in excess of 100 for formic acid formation from methane have been obtained at reaction temperatures below about 100° C. using palladium catalyst. A coreductant of carbon monoxide in an aqueous system is preferred.

26 Claims, No Drawings

OTHER PUBLICATIONS dium Oxide in the Oxidation of Ethane in Acetic Acid, New Developments in Selective Oxidation by Heterogeneous Catalysis; Studies in Surface Science and Catalysis, Ruiz, P. and Delmon, R., Eds., vol. 72, pp. 165–179, (1992).

Thomas, C. L., Catalytic Processes and Proven Catalysts, Academic, New York, 104, (1970).

Happel, J., Study of Kinetic Structure Using Marked Atoms, Catal. Rev., 6, (2), 221–260, (1972).

Laine, R. M., and Wilson, Jr., R. B., Recent Developments in the Homogeneous Catalysis of the Water—Gas Shift Reaction, in Aspects of Homogeneous Catalysis, Ugo, R., Ed., D. Reidel, Dordrecht, 5, 217–240, (1984).

Ford, P. C., The Water Gas Shift Reaction: Homogeneous Catalysis by Ruthenium and Other Metal Carbonyls, Acc. Chem. Res., 14, 2, 31–37, (1981).

Fu, L., Chuang, K. T. and Fiedorow, R., Selective Oxidation of Hydrogen to Hydrogen Peroxide, New Developments in Selective Oxidation by Heterogeneous Catalysis; Studies in Surface Science and Catalysis, Ruiz, P. and Delmon, B., Eds., vol. 72, pp. 33–41, (1992).

Nicoletti, J. W. and Whitesides, G. M., Liquid—Phase Oxidation of 2-Propanol to Acetone by Dioxygen Using Supported Platinum Catalysts, J. Phys., Chem., 93, 759–767, (1989).

Sen A. and Lin, M., A Novel Hybfrid System for the Direct Oxidation of Ethane to Acetic and Glycolic Acids in Aqueous Medium, J. Chem. Soc., Chem. Commun., 6, 508–510, (1992).

Sen, A., Lin, M., Kao, L. C., and Hutson, A. C., J. Am. Chem. Soc. 114, 6385, (1992).

Jones, W. D., Development of Catalytic Processes for the Synthesis of Organic Compounds the Involve C—H Bond Activation, Chap. 5, 113–148, Selective Hydrocarbond Activation, Principles and Progress, Edited by Davies, J. A., Watson, P. L., Greenberg, A. and Lichman, J. F., VCH, (1990).

Lin, M. and Sen, A., A Highly Catalytic System for the Direct Oxidation of Lower Alkanes by Dioxygen in Aqueous Medium. A Formal Heterogeneous Analog of Alkane Monooxtgenases, J. Am. Chem. Soc., 114, 7307–7308, (1992).

Kunai, A, Wani, T, Uehara, Y, Iwasaki, Kuroda, Y, Ito, S, and Sasaki, K., Catalytic Oxidation of Benzene. Catalyst Design and Its Performance, Bull. Chem. Soc. Jpn., 62, 2613–2617, (1989).

Kuroda, Y., Kunaai, A., Hamada, M., Kitano, T., Ito, S. and Sasaki, K., Catalytic Oxidation of Naphthalene on Palladium in Cooperation with Copper (I)/(II) Redox Couple, Bull. Chem. Soc., Jpn., 64, 3089–3093, (1991).

Groh, S. E. and Nelson, M. J., Mechanisms of Activation of Carbon—Hydrogen Bonds by Metalloenzymes, Chap. 10, 305–378, in Selective Hydrocarbon Activation, Davies, J. A., Watson, P. L., Liebman, J. F., Greenberg, A., Eds. VCH, New York, (1990).

Ortiz de Montellano, P. R., Oxygen Activation and Transfer, Chap. 7, 217–271, in Cytochrome P-450: Structure, Mechanism and Biochemistry, Ortiz de Montellano, P. R., Ed., Plenum, New York, (1986).

Guengerich, F. P. and MacDonald, T. L., Chemical Mechanisms of Catalysis by Cytochromes P-450: A Unified View, Acc. Chem. Res., 17, 9–16, (1984).

Groves, J. T., Key Elements of the Chemistry of Cytochrome P-450, J. Chem. Ed., 62, 11, 928–931, (1985).

Walling, C., Fenton's Reagent Revisited, Acc. Chem. Res., 8, 125–131, (1975).

Bakak, A. and Espenson, J. H., Kinetics of the Capture of Methyl Radicals by Carbon Monoxide in Aqueous Solution, J. Chem. Soc., Chem. Commun., 21, 1497–1498, (1991).

Lin, M. and Sen, A., Oxidation and Oxidative Carbonylation of Methane and Ethane by Hexaoxo-$\mu$-peroxodifulfate (2-) Ion in Aqueous Medium, J. Chem. Soc., Chem. Commun. 12, 892–893, (1992).

Kung, H. H., Selective Oxidation Catalysis II, Stud. Surf. Sci. Catal., 45, 200–226, (1989).

CATALYTIC DIRECT OXIDATION OF HYDROCARBONS TO ACIDS

BACKGROUND OF THE INVENTION

1. Field of the Invention

This invention relates to a process for direct oxidation of hydrocarbons, particularly lower alkanes and benzene, to acids by dioxygen under mild temperature conditions using certain metallic or metallic salt catalysts, particularly metallic palladium or platinum or $RhCl_3$ or $CuSO_4$ metallic salt catalysts. Turnovers in excess of 1000 for acetic acid formation from ethane and in excess of 100 for formic acid formation from methane have been observed at reaction temperatures below about 100° C.

2. Description of Related Art

A number of processes for oxidation of unsaturated hydrocarbons are known, for example: U.S. Pat. No. 2,926,191 teaching oxidation of $C_4$–$C_6$ paraffins with $O_2$ without any catalyst to produce acetic acid; U.S. Pat. No. 4,739,107 teaching reaction of an unsaturated hydrocarbon, alcohol and CO over Pd or Pt at 20° to 200° C., with $O_2$ optionally present, to form dicarboxylate esters; U.S. Pat. Nos. 4,681,707 and 4,665,213 teaching similar reactions as the U.S. Pat. No. 4,739,107 with the additional requirement of the catalyst including copper, and teaching substitution of water for the alcohol reactant to produce the corresponding carboxylic acids; U.S. Pat. No. 4,414,409 teaching reaction of an unsaturated hydrocarbon, carbon monoxide and a hydroxylic compound in the presence of a catalyst of an organic phosphine liganded palladium compound and perfluorosulfonic acid to produce corresponding acids and esters; U.S. Pat. No. 3,876,694 teaching oxycarbonylation of olefins to form corresponding acids in a non-aqueous medium using a catalyst system of aluminum, boron or an alkaline earth metal and a compound of palladium which is soluble in the reaction medium; and U.S. Pat. No. 4,469,886 teaching hydrocarboxylation of propylene with carbon monoxide and water to produce isobutyric acid using a catalyst of palladium, a phosphoamine promoter ligand compound and a hydrogen halide.

Catalytic oxidation of saturated hydrocarbons, such as alkanes, requiring C-H activation is a very different and difficult chemical challenge, and one of great practical importance. The lower alkanes of 1 to about 6 carbon atoms are most abundant and least reactive of the alkanes, with methane being the most abundant and least reactive, having a C-H bond energy of 104 kcal/mol, with ethane being second in both categories. A number of processes have been described for such oxidations but they each suffer from requirement of high temperature and/or low turnovers of less than about 10: Baerns, M., van der Wiele, K., and Ross, J. R. H., Methane Activation—A Bibliography, Catal. Today, 4, 471–494, (1989); Pitchai, R. and Klier, K., Partial Oxidation of Methane, Catal. Rev.-Sci. Eng., 28(1), 13–88, (1986); Kung, H. H., Selective Oxidation Catalysis II, Stud. Surf. Sci. Catal., 45, 200–226, (1989); Hunter, N. R., Gesser, H. D., Morton, L. A., Yarlagadda, P. S., and Fung, D. P. C., Methanol Formation at High Pressure by the Catalyzed Oxidation of Natural Gas and by the Sensitized Oxidation of Methane, Appl. Catal., 57, 45–54, (1990); Burch, R., Squire, G. D., Tsang, S. C., Direct Conversion of Methane into Methanol, J. Chem. Soc., Faraday Trans. 1, 85(10), 3561–3568, (1989); Kowalak, S. and Moffat, J. B., Partial Oxidation of Methane Catalyzed by H-Mordenite and Fluorinated Mordenite, Appl. Catal., 36, 139–145, (1988); Stolarov, I. P., Vargaftik, M. N., Shishkin, D. I., and Moiseev, I. I., Oxidation of Ethane and Propane With Co(II) Catalyst, J. Chem. Soc., Chem. Commun., 938–939, (1991); Vargaftik, M. N., Stolarov, I. P., and Moiseev, I. I., Highly Selective Partial Oxidation of Methane to Methyl Trifluoroacetate, J. Chem. Soc., Chem. Commun., 1049–1050, (1990); Herron, N., The Selective Partial Oxidation of Alkanes Using Zeolite Based Catalysts, New J. Chem., 13, 761–766, (1989); and Lyons, J. E., Ellis, Jr., P. E., and Durante, V. A., Active Iron Oxo Centers for the Selective Oxidation of Alkanes, Stud. Surf. Sci. Catal., 67, 99–116, (1991). The Lyons, et al reference, supra, strives to achieve a one-step route to oxidation of lower alkanes to alcohols using iron oxo complexes as catalysts. The oxidation of lower alkanes with $O_2$ catalyzed by azide-activated Group IV(a) to VIII transition metal coordination complexes is taught by U.S. Pat. No. 4,895,682. One well known disadvantage of such coordination complexes is their tendency to degrade under oxidative conditions. Mercury catalyzed oxidation of methane to methanol under mild conditions is taught by Periana, R. A., Taube, D. J., Evitt, E. R., Loffler, D. G., Wentrcek, P. R., Voss, G. and Masuda, T., A Mercury-Catalyzed, High-Yield System for the Oxidation of Methane to Methanol, Science, 259, pp. 340–343, (1993). Low temperature reaction of methane with chlorine in the presence of platinum chlorides and in-situ hydrolyzation of the formed methyl chloride to methanol is taught by Horvath, I. T., Cook, R. A., Millar, J. M. and Kiss, G., Low-Temperature Methane Chlorination with Aqueous Platinum Chlorides in the Presence of Chlorine, Organometallics, 12, pp. 8–10, (1993). Catalytic oxidation of ethane to acetic acid at temperatures above about 250° C. using promoted vanadium oxide catalysts is taught by Merzouki, M., Taouk, B., Monceaux, L., Bordes, E. and Courtine, P., Catalytic Properties of Promoted Vanadium Oxide in the Oxidation of Ethane in Acetic Acid, New Developments in Selective Oxidation by Heterogeneous Catalysis; Studies in Surface Science and Catalysis, Ruiz, P and Delmon, B., Eds., Vol. 72, pp. 165–179, (1992).

Metal-catalyzed water-gas-shift reactions are known as exemplified by: Thomas, C. L., Catalytic Processes and Proven Catalysts, Academic, New York, 104, (1970); Happel, J., Study of Knietic Structure Using Marked Atoms, Catal. Rev., 6,(2), 221–260, (1972); Laine, R. M., and Wilson, Jr., R. B., Recent Developments in the Homogeneous Catalysis of the Water-Gas Shift Reaction, in Aspects of Homogeneous Catalysis, Ugo, R., Ed., D. Reidel, Dordrecht, 5, 217–240, (1984); and Ford, P. C., The Water Gas Shift Reaction: Homogeneous Catalysis by Ruthenium and Other Metal Carbonyls, Acc. Chem. Res., 14, 2, 31–37, (1981).

The catalytic formation of hydrogen peroxide from dihydrogen and dioxygen using palladium on absorbent carbon is taught by U.S. Pat. No. 4,681,751. The selective oxidation of hydrogen to hydrogen peroxide by palladium on a hydrophobic support is taught by Fu, L., Chuang, K. T. and Fiedorow, R., Selective Oxidation of Hydrogen to Hydrogen Peroxide, New Developments in Selective Oxidation by Heterogeneous Catalysis; Studies in Surface Science and Catalysis, Ruiz, P. and Delmon, B., Eds., Vol. 72, pp 33–41, (1992).

The oxidation of 2-propanol to acetone by dioxygen has been reported by Nicoletti, J. W. and Whitesides, G. M., Liquid-Phase Oxidation of 2-Propanol to Acetone by Dioxygen Using Supported Platinum Catalysts, J. Phys. Chem., 93, 759–767, (1989).

Metal catalyzed oxidation of alcohol to carboxylic acid requiring a divalent platinum complex for the initial oxidation step is taught by Sen, A. and Lin, M., A Novel Hybrid System for the Direct Oxidation of Ethane to Acetic and Glycolic Acids in Aqueous Medium, J. Chem. Soc., Chem. Commun., 6, 508–510, (1992) and Sen, A., Lin, M., Kao, L. C., and Hutson, A. C., J. Am. Chem. Soc. 114, 6385, (1992).

The partial oxidation of methane in a motored engine at 650° to 800° C. and under compression of 20/1 to 60/1 without any catalyst to form small amounts of oxygenated products is taught by U.S. Pat. No. 2,922,809.

The formation of acetic acid from methane and carbon dioxide and the formation of acetaldehyde from methane and carbon monoxide by addition reactions in the presence of a metal catalyst such as palladium or platinum or their carbonates is taught by U.S. Pat. No. 1,916,041. It must be noted that there is no net oxidation in the reactions taught by the U.S. Pat. No. 1,916,041. Further, the addition reactions referred to in U.S. Pat. No. 1,916,041 are thermodynamically uphill and cannot proceed except to produce trace amounts of the products as set forth by Jones, W. D., Development of Catalytic Processes for the Synthesis of Organic Compounds the Involve C-H Bond Activation, Chap. 5, 113–148, Selective Hydrocarbond Activation, Principles and Progress, Edited by Davies, J. A., Watson, P. L., Greenberg, A. and Lichman, J. F., VCH, (1990).

SUMMARY OF THE INVENTION

It is an object of this invention to provide a process for catalytic oxidation of hydrocarbon compounds to acids by dioxygen under mild conditions.

It is another object of this invention to provide a process for catalytic direct oxidation of lower alkanes and single ring aromatic compounds to corresponding acids, particularly methane and ethane to principally formic and acetic acid, respectively, at temperatures below about 200° C.

Another object of this invention is to provide a process for catalytic direct oxidation of lower alkanes to high yields of the corresponding acid by dioxygen using a palladium catalyst.

Yet another object of this invention is to provide a catalytic process for high conversion of lower alkanes to principally the corresponding acid in an aqueous system.

Still another object of this invention is to provide a process for catalytic conversion of benzene and other aromatic hydrocarbons to principally formic acid under mild conditions.

These and other objects and advantages of the invention are achieved in one embodiment of the invention by contacting the hydrocarbon material, particularly lower alkanes and benzene, with hydrogen peroxide in the presence of a metallic catalyst selected from the group consisting of iron, ruthenium, osmium, cobalt, rhodium, iridium, nickel, palladium, platinum, copper, silver and gold and their salts, at a temperature of about 700° to about 200° C. to produce the corresponding acid. In this embodiment, the hydrogen peroxide should be added to the process at about the rate at which the hydrocarbon material is converted to the acid, thereby preventing substantial excesses of hydrogen peroxide from being present. In another embodiment, hydrogen peroxide may be formed at the desired rate for reaction by contacting dihydrogen and dioxygen under acidic conditions producing hydrogen peroxide and contacting the formed hydrogen peroxide and a hydrocarbon material to produce the corresponding acid, each of the contacting steps being conducted in the presence of a metallic catalyst as set forth above and at a temperature of about 70° to about 200° C. in an aqueous or a non-aqueous medium.

In one preferred embodiment for catalytic oxidation of a lower alkane to acid in a single reaction system, carbon monoxide and water are contacted under acidic conditions producing carbon dioxide and dihydrogen, then the formed dihydrogen and dioxygen are contacted under acidic conditions producing hydrogen peroxide, and then the formed hydrogen peroxide and lower alkane are contacted producing the corresponding acid, each of the contacting being performed in the presence of a metallic catalyst selected from the group consisting of palladium and platinum and at a temperature of about 70° to about 110° C.

Portions of this invention have been described by the inventors in Lin, M. and Sen, A., A Highly Catalytic System for the Direct Oxidation of Lower Alkanes by Dioxygen in Aqueous Medium. A Formal Heterogeneous Analog of Alkane Monooxtgenases, J. Am. Chem. Soc., 114, 7307–7308, (1992), which is incorporated herein in its entirety by reference.

DESCRIPTION OF PREFERRED EMBODIMENTS

The process of this invention is applicable to the catalytic direct oxidation of hydrocarbons to acids by dioxygen under mild temperature conditions. A wide range of hydrocarbon materials are suitable for use in the process of this invention. Saturated and unsaturated aliphatic hydrocarbons, straight chain, branched chain and cyclic, as well as aromatic materials having one or multiple benzene rings are suitable for use in the process of this invention. The process of this invention is particularly suited to direct oxidation of lower alkanes having 1 to about 6 carbon atoms and single ring aromatic hydrocarbons to acids by dioxygen. Methane, ethane, propane, butane, isopropane, isobutane and benzene are preferred hydrocarbon reactants in the process of this invention.

Suitable metallic catalysts for the process of this invention include Fe, Ru, Os, Co, Rh, Ir, Ni, Pd, Pt, Cu, Ag and Au which may be used in metallic form on a suitable support. Salts of these metals which are soluble in the reaction medium may also be used as catalysts, such as, $RhCl_3$ and $CuSO_4$.

In one preferred embodiment of the invention, the metal serves as catalyst for three reactions in tandem resulting in the oxidation of the hydrocarbon reactant and the coreductant (carbon monoxide) and the reduction of dioxygen. While the detailed mechanism is not presently understood, the overall transformation appears to involve three catalytic reactions in tandem. These may be somewhat analogous to the mechanistic pathway in the recently described aromatic oxidations by the Pd metal/$Cu^{II}$/$H_2$/$O_2$ system as described in Kunai, A, Wani, T, Uehara, Y, Iwasaki, Kuroda, Y, Ito, S, and Sasaki, K., Catalytic Oxidation of Benzene. Catalyst Design and Its Performance, Bull. Chem. Soc. Jpn., 62, 2613–2617, (1989) and Kuroda, Y., Kunaai, A., Hamada, M., Kitano, T., Ito, S. and Sasaki, K., Catalytic Oxidation of Naphthalene on Palladium in Cooperation with Copper(I)/(II)Redox Couple, Bull. Chem. Soc. Jpn., 64, 3089–3093, (1991). The requirement of a coreductant makes the overall reaction formally analogous to the reaction of monooxygenases in which only one of the two oxygen atoms in the dioxygen molecule is utilized for substrate oxidation as described in Groh, S. E. and Nelson, M. J., Mechanisms of Activation of Carbon-Hydrogen Bonds by Metalloenzymes, Chap. 10, 305–378, in Selective Hydrocarbon Activation, Davies, J. A., Watson, P. L., Liebman, J. F., Greenberg, A., Eds. VCH, New York, (1990), Ortiz de Montellano, P. R., Oxygen Activation and Transfer, Chap. 7, 217–271, in Cytochrome P-450: Structure, Mechanism and Biochemistry, Ortiz de Montellano, P. R., Ed., Plenum, N.Y., (1986), Guengerich, F. P. and MacDonald, T. L., Chemical Mechanisms of Catalysis by Cytochromes P-450: A Unified View, Acc. Chem. Res., 17, 9–16, (1984), and Groves, J. T., Key Elements of the Chemistry of Ctochrome P-450, J. Chem. Ed., 62, 11, 928–931, (1985).

We have found that in this embodiment both carbon monoxide and an acidic solution are necessary since little or no oxidation occurred in their absence. In the process of this invention, we have found that dioxygen alone is ineffective, thereby indicating that the active surface metal species generated when using hydrogen peroxide must be different from any that may form through reaction with dioxygen. Since free alkyl radicals do not appear to be intermediates, due to the absence of products derived from trapping by carbon monoxide, the role of the metal cannot be to simply initiate Fenton-type chemistry through O—O bond cleavage of hydrogen peroxide as described in Walling, C., Fenton's Reagent Revisited, Acc. Chem. Res., 8, 125–131, (1975). The mechanism is supported by the fact use of $^{13}CO$ resulted in formation of $^{13}CO_2$ as the only $^{13}C$-containing product as determined by $^{13}C$ NMR. Water was also necessary since no oxidation was observed in a dry $CH_3NO_2/CF_3CO_2H$ mixture.

It is possible to bypass the first catalytic reaction by replacing carbon monoxide with dihydrogen. In this instance it is possible to conduct the reaction in a nonaqueous medium such as polar organic solvents, for example, nitromethane, acetonitrile, dimethyl sulfoxide and similar polar solvents. In one instance this may be described by the following chemical equation:

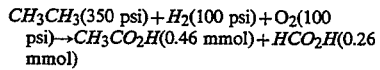

$CH_3CH_3(350\ psi) + H_2(100\ psi) + O_2(100\ psi) \rightarrow CH_3CO_2H(0.46\ mmol) + HCO_2H(0.26\ mmol)$ conducted in a medium $CH_3NO_2$(3 ml)/$CF_3CO_2H$(0.08 ml) in contact with a catalyst 5% Pd/C (50 mg), at 85° C. for 12 hours.

We found that the second catalytic reaction involving the formation of hydrogen peroxide from dihydrogen and dioxygen proceeded only under acidic conditions. The formation of hydrogen peroxide in the system starting with carbon monoxide and dioxygen in the presence of water was verified by running the reaction in the absence of alkane. Titration of the product with a standard solution of $KMnO_4$ showed a hydrogen peroxide concentration of 0.002M. In the system starting with carbon monoxide, hydrogen peroxide was formed at a low, steady rate through the first two catalytic reactions. This rate of formation of hydrogen peroxide provided efficient use for alkane oxidation. On the other hand, when starting with dihydrogen, hydrogen peroxide was formed rapidly, as evidenced by rapid drop is gas pressure, and most of the product hydrogen peroxide underwent subsequent metal-catalyzed decomposition at reaction temperatures of 85° to 100° C., making it unavailable for alkane oxidation.

In the oxidation of ethane, a significant amount of formic acid has been observed to be formed through a further oxidation step involving C—C bond cleavage. Free methyl radical, which might be formed by a possible decarboxylation step, did not appear to be an intermediate in this reaction since, in the presence of $^{13}CO$, $CH_3{}^{13}CO_2H$ was not observed as a product. Carbon monoxide is an efficient trapping agent for the methyl radical, having a rate constant in water of $2 \times 10^6$ L mol$^{-1}$s$^{-1}$ at 25° C. Bakak, A. and Espenson, J. H., Kinetics of the Capture of Methyl Radicals by Carbon Monoxide in Aqueous. Solution, J. Chem. Soc., Chem. Commun., 21, 1497–1498, (1991) We have previously observed formation of acetic acid in good yields from methyl radical and carbon monoxide in water under oxidizing conditions. Lin, M. and Sen, A., Oxidation and Oxidative Carbonylation of Methane and Ethane by Hexaoxo-$\mu$-peroxodifulfate(2-)Ion in Aqueous Medium, J. Chem. Soc., Chem. Commun. 12, 892–893, (1992). In the process of this invention, the further oxidation of acetic acid also required the presence of carbon monoxide, therefore, hydrogen peroxide, in the system and did not occur in the presence of only dioxygen.

When using the process of this invention for the oxidation of methane to formic acid, we have found that the formic acid was less stable than the acetic acid, being more prone to decomposition to carbon monoxide and water and overoxidation to carbon dioxide and water. However, we have found that we could obtain turnovers corresponding to formic acid formation in the range of 60 to 160.

The catalytic oxidation according to this invention of a hydrocarbon material by dioxygen to an acid, such as a lower alkane produces principally its corresponding acid and a single ring aromatic material produces principally formic acid. By the terminology principally, we mean that over fifty percent of the product is the corresponding acid. However, generally over at least about sixty to seventy percent of the product is the corresponding acid. The hydrocarbon material is contacted with hydrogen peroxide, the hydrogen peroxide being provided to the process at about the rate at which the hydrocarbon reactant is converted to the acid, thereby preventing excesses of the hydrogen peroxide from being present in the reaction system. The contacting is carried out in the presence of a metallic catalyst as set forth above. Metallic Pd and Pt and salts $RhCl_3$ and $CuSO_4$ are preferred catalysts. Palladium is a particularly preferred metallic catalyst, providing the highest catalytic activity. The catalyst may be in any suitable form providing good surface contact with the hydrocarbon and hydrogen peroxide for reaction. The metallic catalyst may be on a suitable support material, such as, carbon, alumina, silica, titania and zirconia. Especially preferred is palladium on carbon in an amount of about 40 to about 80 $\mu$mol surface palladium atoms per gram of catalyst. Catalytic activity may be expressed as turnovers corresponding to the desired product formation obtained by dividing the mmol of desired product formed by mmol of surface metal atoms which may be determined by chemisorption methods. Salts of the metallic catalyst which are soluble in the reaction media may be used, such as $RhCl_3$ and $CuSO_4$. The contacting is carried out at temperatures of about 70° to about 200° C., preferably about 70° to about 110° C. High catalytic direct oxidation of lower alkanes at such moderate temperatures is one advantage of the process of this invention, for example, starting with ethane, it is possible to form acetic acid having a concentration exceeding 0.5M. Turnovers corresponding to acetic acid formation from ethane using preferred embodiments of this invention are in the range of about 900 to about 1100, while turnovers corresponding to formic acid formation for methane are in the range of about 80 to about 160.

Hydrogen peroxide may be fed to the reaction system at a desired rate to provide hydrogen peroxide for reaction without having undesired excesses present in the reaction system. Hydrogen peroxide may also be formed in the reaction system at the desired rate by contacting dihydrogen and dioxygen under acidic conditions in the presence of the same catalysts and at the same temperatures as described above for contacting the hydrogen peroxide and hydrocarbon. In this embodiment, an aqueous or non-aqueous reaction medium may be used. However, in this embodiment the rate of hydrogen peroxide formation should be controlled so that its rate of production is not greatly in excess or is about the rate at which the hydrocarbon is converted to acid, thereby preventing substantial excesses of hydrogen peroxide in the reaction system. When there is an excess of hydrogen peroxide in the reaction system, it will undergo metal catalyzed decomposition at the temperatures of the reaction system.

In a preferred reaction system according to this invention we have found that first contacting carbon monoxide and water under acidic conditions producing carbon dioxide and dihydrogen, then contacting the formed dihydrogen and dioxygen under acidic conditions producing hydrogen peroxide, followed by contacting the formed hydrogen peroxide and hydrocarbon material to produce the corresponding acid, each of the contacting steps being performed in the presence of a metallic catalyst set forth above and at a temperature of about 70° to about 200° C. results in highly efficient catalytic oxidation of the hydrocarbon to principally the corresponding acid. The above reactions using the same catalyst and temperature conditions for the series of three reactions provides a single reaction system which may be conducted in a single pass over a single catalyst composition in a single reaction vessel. In this single reaction system, hydrogen peroxide is formed at a low, steady rate through the first two reactions and used efficiently for hydrocarbon oxidation in the third tandem reaction.

The following examples illustrate specific aspects of the invention using specific reactants and reaction conditions and should not be considered as limiting the invention in any manner.

EXAMPLE I

Ethane was catalytically oxidized to produce principally acetic acid in high yields using one preferred embodiment of the process of this invention. 5 ml of 0.1M DCl in $D_2O$; CO at 100 psi; $O_2$ at 100 psi; and $CH_3CH_3$ at 500 psi; were contacted over a catalyst bed of 40 mg of 5% palladium on carbon, 60 μmol surface Pd atoms per gram catalyst, for 20–24 hours at the indicated temperatures. The reactions were carried out in 140 ml glass lined stainless steel bombs. About 180 mmol of $CH_3CH_3$ was present in the original gas mixture. Product yields were determined independently by $^1H$ nuclear magnetic resonance and gas chromotography. The amount of surface metal atoms in the catalyst was determined by dihydrogen chemisorption studies. The number of turnovers corresponding to each product formed is expressed by the relation mmol of product/mmol of surface metal atoms of catalyst. The results of runs at various temperatures is shown in Table 1.

TABLE 1

| Temp., °C. | Yield, mmol (turnover) | | |
|---|---|---|---|
| | $CH_3CO_2H$ | $HCO_2H$ | $CH_3CH_2OH$ |
| 70 | 0.53 (221) | 0.12 (50) | 0.035 (15) |
| 85 | 2.55 (1063) | 1.43 (596) | |
| 100 | 2.73 (1138) | 0.24 (100) | |
| 110 | 0.88 (367) | 0.16 (67) | |

EXAMPLE II (Comparative)

The process was conducted as described in Example I at 100° C. without adding CO and resulted in production of 0.001 mmol $CH_3CO_2H$.

EXAMPLE III (Comparative)

The process was conducted as described in Example I at 100° C. without adding DCl and resulted in production of 0.006 mmol $CH_3CO_2H$.

EXAMPLE IV

The process was conducted as described in Example I except that it was conducted at 95° C. using 10.6 mg of palladium black as a catalyst and resulted in production of 0.30 mmol of each $CH_3CO_2H$ and $HCO_2H$.

EXAMPLE V

The process was conducted as described in Example I except that it was conducted at 95° C. using 40 mg of 5% palladium on alumina, 114 μmol of surface Pd atoms per gram of catalyst, as a catalyst and resulted in production of 0.40 mmol of $CH_3CO_2H$ with a turnover of 88 and 0.11 mmol of $HCO_2H$ with a turnover of 24.

EXAMPLE VI

The process was conducted as described in Example I except that it was conducted at 95° C. using 50 mg of 5% platinum on carbon as a catalyst and resulted in production of 0.13 mmol of $CH_3CO_2H$.

EXAMPLE VII

The process was conducted as described in Example I except that 21 mg (0.1 mmol) $RhCl_3$ was used as catalyst and the partial pressure of CO was 200 psi. The reaction was carried out at 95° C. for 49 hours and resulted in production of 0.029 mmol $CH_3CH_2OH$, 0.008 mmol $CH_3CO_2H$ and 0.009 mmol $CH_3CH_2CO_2H$. The combined yield of these three products was 46.0 percent based on $RhCl_3$.

EXAMPLE VIII

The process was conducted as described in Example I except that 20 mg (0.125 mmol) $CuSO_4$ was used as catalyst, 4 ml of 0.1M DCl in $D_2O$ was used and the partial pressure of CO was 200 psi. The reaction was carried out at 95° C. for 18 hours and resulted in production of 0.408 mmol $CH_3CO_2H$ (turnover of 3.3), 0.036 mmol $CH_3OH$ and 0.018 mmol $CH_3CH_2OH$.

EXAMPLE IX

Methane was catalytically oxidized to produce principally formic acid in high yields by the process described in Example I except that $CH_4$ at 800 psi was substituted for $CH_3CH_3$, 20 mg of 5% Pd on carbon was used and the reaction was carried out at 85° C. for 18 hours. The yield of formic acid was 0.165 mmol with turnover of 140. The product formic acid was less stable in the catalytic system, being prone to decomposition to CO and $H_2O$ and overoxidation to $CO_2$ and $H_2O$.

EXAMPLE X

The process was conducted as described in Example IX except increasing partial pressure of CO to 200 psi resulted in production of 0.10 mmol formic acid with turnover of 84.

EXAMPLE XI

The process was conducted as described in Example IX except that the reaction was run at 45° C. for 48 hours and resulted in production of 0.143 mmol formic acid with turnover of 120.

EXAMPLE XII

The process was conducted as described in Example IX except that the reaction was run at 100° C. for 40 hours and resulted in production of 0.060 mmol formic acid.

EXAMPLE XIII

Benzene was catalytically oxidized to produce principally formic acid by the process described in Example I except that 40μl of $C_6H_6$ (0.45 mmol) was substituted for $CH_3CH_3$ and the reaction was carried out at 85° C. for 24 hours. The oxidative products were 0.16 mmol formic acid; 0.023 mmol phenol; 0.019 mmol. glycolic acid; 0.011 mmol 1,4-Benzoquinone; and a small amount of $CH_2(OH)_2$.

EXAMPLE XIV

The process was conducted as described in Example XIII except that 50 μl $^{13}C_6H_6$ (0.48 mmol), CO at 200 psi and $O_2$ at 200 psi were used and the reaction conducted for 30 hours. The principal oxidative products were $H^{13}CO_2H$ (0.18 mmol) and $HO^{13}CH_2^{13}CH_2OH$ (0.013 mmol)

EXAMPLE XV

The process was conducted as described in Example XIII except the reaction was carried out at 70° C. for 18 hours. The oxidative products were formic acid (0.22 mmol), phenol (0.13 mmol), glycolic acid (0.050 mmol), 1,4-Benzoquinone (0.014 mmol) and a small amount of $CH_2(OH)_2$.

EXAMPLE XVI

The process was conducted as described in Example XIII except the reaction was carried out at 90° C. for 12 hours. The oxidative products were formic acid (0.18 mmol), phenol (0.078 mmol), 1,4-Benzoquinone (0.037 mmol), glycolic acid (0.010 mmol) and a small amount of $CH_2(OH)_2$.

EXAMPLE XVII

Phenol was catalytically oxidized to produce principally formic acid by the process described in Example XIII except that 40 mg of phenol (0.43 mmol) was substituted for $C_6H_6$ and the reaction carried out at 70° C. for 36 hours. The oxidative products were formic acid (0.11 mmol), 1,4-Benzoquinone (0.082 mmol); glycolic acid (0.014 mmol) and a small amount of $CH_2(OH)_2$.

EXAMPLE XVIII 1,4-Benzoquinone was catalytically oxidized to produce principally formic acid by the process described in Example XIII except that 40 mg of 1,4-Benzoquinone (0.37 mmol) was substituted for $C_6H_6$ and the reaction carried out at 80° C. for 3 days. The oxidative products were formic acid (0.11 mmol), glycolic acid (0.014 mmol) and a small amount of $CH_2(OH)_2$.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. A process for catalytic oxidation of a hydrocarbon selected from the group consisting of an alkane having 1 to about 6 carbon atoms and a single ring aromatic compound to acid comprising contacting said hydrocarbon with hydrogen peroxide in the presence of a metallic catalyst selected from the group consisting of Fe, Ru, Os, Co, Rh, Ir, Ni, Pd, Pt, Cu, Ag and Au and their salts at a temperature about 70° to about 200° C. to principally produce the corresponding acid in the case of said alkane and formic acid in the case of said single ring aromatic compound.

2. A process according to claim 1 wherein said hydrocarbon principally comprises methane.

3. A process according to claim 1 wherein said catalyst is selected from the group consisting of metallic Pd and Pt and soluble salts $RhCl_3$ and $CuSO_4$.

4. A process according to claim 1 wherein said catalyst is palladium.

5. A process according to claim 1 wherein said temperature is about 70° to about 110° C.

6. A process according to claim 1 wherein said hydrogen peroxide is added to said process at about the rate at which said hydrocarbon is converted to said acid, thereby preventing substantial excesses of said hydrogen peroxide from being present.

7. A process according to claim 1 wherein said hydrocarbon is a lower alkane having 1 to about 6 carbon atoms, said catalyst is palladium, said temperature is about 70° to about 110° C., and said hydrogen peroxide is added to said process at about the rate at which said lower alkane is converted to said acid, thereby preventing substantial excesses of said hydrogen peroxide from being present.

8. A process according to claim 7 wherein said lower alkane principally comprises methane.

9. A process according to claim 7 wherein said lower alkane principally comprises ethane to principally produce acetic acid.

10. In a process for catalytic oxidation of a hydrocarbon selected from the group consisting of an alkane having 1 to about 6 carbon atoms and a single ring aromatic compound to acid, the steps comprising: contacting dihydrogen and dioxygen under acidic conditions producing hydrogen peroxide; and contacting said hydrogen peroxide and said hydrocarbon to principally produce the corresponding acid in the case of said alkane and formic acid in the case of said single ring aromatic compound; each of said contacting steps conducted in the presence of a metallic catalyst selected from the group consisting of Fe, Ru, Os, Co, Rh, Ir, Ni, Pd, Pt, Cu, Ag and Au and their salts at a temperature of about 70° to about 200° C.

11. In a process according to claim 10 wherein said process is carried out in a non-aqueous medium.

12. In a process according to claim 10 wherein said hydrocarbon principally comprises methane.

13. In a process according to claim 10 wherein said catalyst is selected from the group consisting of metallic Pd and Pt and soluble salts $RhCl_3$ and $CuSO_4$.

14. In a process according to claim 10 wherein said catalyst is palladium.

15. In a process according to claim 10 wherein said temperature is about 70° to about 110° C.

16. In a process according to claim 10 wherein said hydrogen peroxide is produced at about the rate at which said hydrocarbon is converted to said acid, thereby preventing substantial excesses of said hydrogen peroxide from being present.

17. In a process according to claim 10 wherein said hydrocarbon is a lower alkane having 1 to about 6 carbon atoms, said catalyst is palladium, said temperature is about 70° to about 110° C., and said hydrogen peroxide is produced at about the rate at which said lower alkane is converted to said acid, thereby preventing substantial excesses of said hydrogen peroxide from being present.

18. A process for catalytic oxidation of a hydrocarbon selected from the group consisting of an alkane having 1 to about 6 carbon atoms and a single ring aromatic compound to the corresponding acid in the case of said alkane and formic acid in the case of said single ring aromatic compound comprising in a single reaction system: first contacting carbon monoxide and water under acidic conditions producing carbon dioxide and dihydrogen; then contacting said dihydrogen and dioxygen under acidic conditions producing hydrogen peroxide; and contacting said hydrogen peroxide and said hydrocarbon to produce said acid; each of said contacting steps performed in the presence of a metallic catalyst selected from the group consisting of Fe, Ru, Os, Co, Rh, Ir, Ni, Pd, Pt, Cu, Ag and Au and their salts at a temperature of about 70° to about 200° C.

19. A process according to claim 18 wherein said hydrocarbon principally comprises methane.

20. A process according to claim 18 wherein said catalyst is selected from the group consisting of metallic Pd and Pt and soluble salts $RhCl_3$ and $CuSO_4$.

21. A process according to claim 18 wherein said catalyst is palladium.

22. A process according to claim 18 wherein said temperature is about 70° to about 110° C.

23. A process according to claim 18 wherein said hydrogen peroxide is produced at about the rate at which said hydrocarbon is converted to said acid, thereby preventing substantial excesses of said hydrogen peroxide from being present.

24. A process according to claim 18 wherein said hydrocarbon is a lower alkane having 1 to about 6 carbon atoms, said catalyst is palladium, said temperature is about 70° to about 110° C., and said hydrogenperoxide is produced at about the rate at which said lower alkane is converted to said acid, thereby preventing substantial excesses of said hydrogen peroxide from being present.

25. A process according to claim 18 wherein said hydrocarbon principally comprises ethane to principally produce acetic acid.

26. A process according to claim 18 wherein said process is carried out in a non-aqueous medium.

* * * * *